United States Patent [19]

Nakamura

[11] Patent Number: 5,713,545
[45] Date of Patent: Feb. 3, 1998

[54] STAND APPARATUS FOR MEDICAL OPTICAL EQUIPMENTS

[75] Inventor: Katsushige Nakamura, Tokyo, Japan

[73] Assignee: Mitaka Kohki Co. Ltd., Tokyo, Japan

[21] Appl. No.: 571,430

[22] Filed: Dec. 13, 1995

[51] Int. Cl.$^6$ ........................................... F16L 3/00
[52] U.S. Cl. ........................ 248/123.2; 248/280.11; 359/384
[58] Field of Search ................. 248/123.1, 200.1, 248/325, 648, 665, 292.1, 281.1; 359/368, 384

[56] References Cited

U.S. PATENT DOCUMENTS

| | | | |
|---|---|---|---|
| 3,891,301 | 6/1975 | Heller | 350/85 |
| 4,339,100 | 7/1982 | Heller et al. | 248/123.1 |
| 4,548,373 | 10/1985 | Komura | 248/122 |
| 5,243,370 | 9/1993 | Slater | 352/243 |

FOREIGN PATENT DOCUMENTS 56-32110  4/1981  Japan.

*Primary Examiner*—Ramon O. Ramirez
*Assistant Examiner*—Willie Berry, Jr.
*Attorney, Agent, or Firm*—Michael D. Bednarek; Kilpatrick Stockton LLP

[57] ABSTRACT

Disclosed is a medical optical devices wherein balance in a horizontal direction can be adjusted by moving the counterweight horizontally, and the balance in a vertical direction can be adjusted by moving whole the retaining link mechanism vertically. Thus only one counterweight is required, which eliminates a need to interlockedly move two counterweights simultaneously as conventionally, so that movement control of a counterweight is easy and a mechanism therefor can be simplified.

12 Claims, 2 Drawing Sheets

STAND APPARATUS FOR MEDICAL OPTICAL EQUIPMENTS

BACKGROUND OF THE INVENTION

1. Field of the Invention

This invention relates to a stand in which heavy medical optical equipments such as an operating microscope and its auxiliary devices are supported can be kept at desired spatial positions during microsurgery.

2. Description of Prior Art

In the fields of encephalotomy and cardiosurgery, a technique of so-called microsurgery is employed, in which surgeries are performed under observation of the focuses using operating microscopes as "medical optical equipments". Various types of stand apparatuses for retaining a heavy operating microscope and its auxiliary devices at any desired spatial positions, to be utilized in such microsurgeries have been proposed (e.g. Laid-open Japanese Patent Publication No. 32110/1981). These stands generally are of a balancing structure, in which a retaining link mechanism employing a parallel link is pivotally (tiltably) supported at an intermediary portion on a frame, and an operating microscope is supported at one end portion of the retaining link mechanism with a counterweight for countervailing the weight of the operating microscope being supported on the other end portion of the retaining link mechanism relative to the pivot thereof.

As a position where the balancing-type stand is set up, an optimum position in an operating room is selected depending on the content of the surgery to be carried out, and balance is adjusted at the selected position. Since auxiliary devices such as a side microscope for assistant doctors and a video camera are attached to the operating microscope, the position of the counterweight is changed corresponding to the weight of these devices to adjust the entire balance of the stand.

In such a stand apparatus, the operating microscope must be perfectly balanced in the horizontal and vertical directions in order to stop the operating microscope and the auxiliary devices at a desired spatial position. However, conventional stands do not always have a structure which facilitates secured balance adjustment in the horizontal and vertical directions in accordance with the weight on the operating microscope side which changes depending on the presence or absence of various auxiliary devices. For eliminating such inconvenience, there have been proposed some types of apparatuses which are moveably provided with two counterweights, one in the horizontal direction and the other in the vertical so that the two counterweights are interlockedly moved to adjust balance both in the horizontal and vertical directions. However, such structures become so complicated and large to simultaneously and interlockedly move the two counterweights, which is not preferable from weight and cost aspects.

This invention has been accomplished noting such prior art technique and is directed to provide a stand apparatus for medical optical equipments, which enables easy and secured balance adjustment with only single counterweight in accordance with the weight change on the operating microscope side.

SUMMARY OF THE INVENTION

In a first mode of the present invention, an intermediary portion of a retaining link mechanism essentially consisting of first and second parallel links which interlock each other is mounted moveably in a vertical direction with respect to a rotational fulcrum of a frame, a part of the above described first parallel link is horizontally extended to form a supporting arm at which extremity medical optical equipments and/or their auxiliary devices are retained, and a part of the above described second parallel link is extended horizontally in a direction opposite to the first parallel link to form a weight holding arm at which extremity moveable counterweight is retained.

According to the first mode, the balance in a horizontal direction can be adjusted by moving the counterweight horizontally, and the balance in a vertical direction can be adjusted by moving whole the retaining link mechanism vertically. Thus only one counterweight is required, which eliminates a need to interlockedly move two counterweights simultaneously as conventionally, so that movement control of a counterweight is easy and a mechanism therefor can be simplified. Since vertical balancing is effected via a movement of the whole retaining link mechanism, even a slight movement can provide an effective balancing control. Therefore, an operation of balancing control is easy and reduced operational time required for balancing control is possible.

In a second mode of the present invention, a weight holding arm is horizontally extended and is provided with a moveable counterweight, and the intermediary portion of the retaining link mechanism is mounted moveably in a horizontal direction with respect to the rotational fulcrum on the frame.

According to the second mode of the invention, balance in a vertical direction can be adjusted by moving the counterweight vertically, and balance in a horizontal direction can be adjusted by moving whole the retaining link mechanism horizontally.

It should be noted that the content of the invention is not limited to the above description, and the objects, advantages, features, and usages will become more apparent according to descriptions below. It is also to be understood that any appropriate changes without departing from the spirit of the invention are in the scope of the invention.

DETAILED DESCRIPTION OF THE PREFERRED EMBODIMENTS

Figure 1:
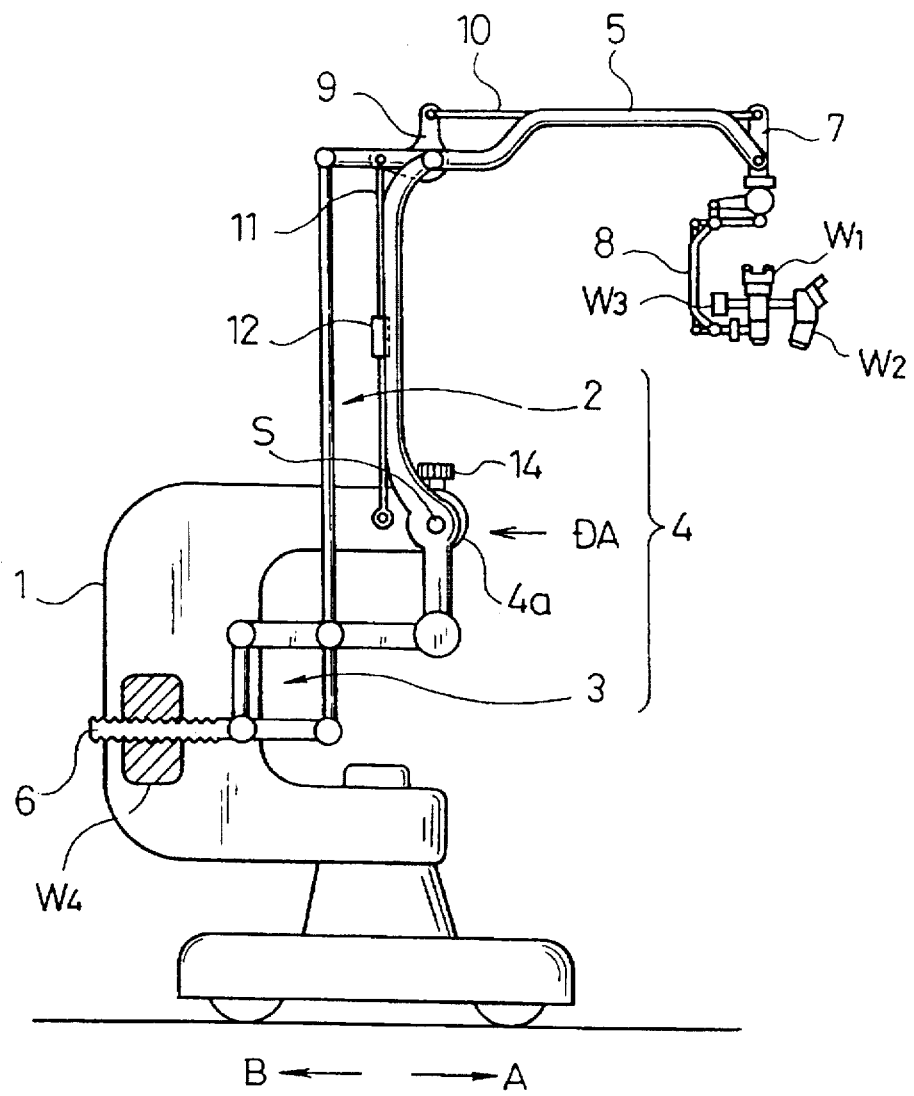
FIG. 1 is a side view showing a stand apparatus for medical optical equipments for according to an embodiment of the invention.
Figure 2:
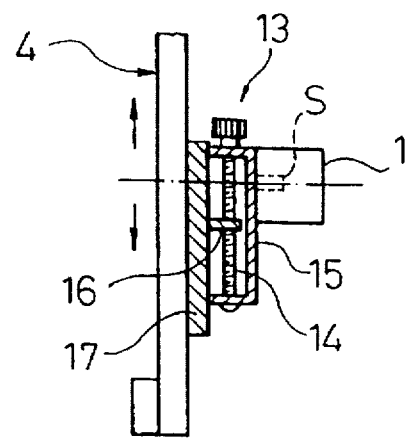
FIG. 2 is a side view in partial section taken in the direction of an arrow DA.
Figure 3:
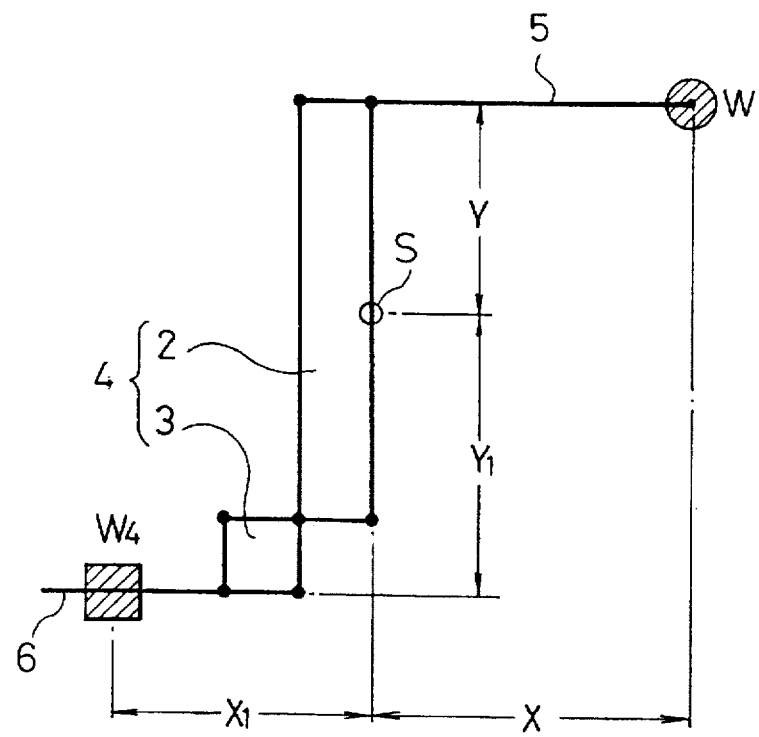
FIG. 3 is an explanatory view showing the total weight of an operating microscope, a side microscope, and a video camera is balanced with a counterweight.

Preferred embodiments of the invention will be described below referring to FIGS. 1 through 4. It should be noted that the following description is made assuming that the arrow A and the arrow B shown in Figure mean the front side and the rear side, respectively.

The stand apparatus according to the preferred embodiment of the invention has a basic structure wherein a retaining link mechanism 4 essentially consisting of a first parallel link 2 and a second parallel link 3 is supported at a part (intermediary portion 4a) on a rotational fulcrum S on a frame 1, and further wherein an operating microscope $W_1$ and other equipments are supported at the extremity of a supporting arm 5 which is a forwardly extended portion of the first parallel link 2, while a counterweight $W_4$ is moveably provided on a weight holding arm 6 which is a rearwardly extended portion of the second parallel link 3. The supporting arm 5 is bulged upward so as not to interfere with the head of the doctor.

The supporting arm 5 pivotally supports at the distal end thereof a vertical distal end arm 7 beneath which is provided a small supporting parallel link 8 wherein two parallel links are interlocked. An operating microscope $W_1$ (a medical optical equipment) is mounted to the lowest part of the supporting parallel link 8. The whole configuration of the supporting parallel link 8 presents curve, so that a doctor is allowed to readily operate the operating microscope $W_1$. The view angle of the operating microscope $W_1$ can be changed by transforming the supporting parallel link 8. The operating microscope $W_1$ is equipped with such "auxiliary devices" as a side microscope $W_2$ for assistant doctors and a video camera $W_3$ for recording, and attaching or detaching these auxiliary devices will change the weight on the operating microscope $W_1$ side.

The connecting point which is the origin of the supporting arm 5 pivotally supports an L-shaped bell crank 9 of which one end is connected to the upper end of the distal end arm 7 via a horizontal subarm 10, and the other end of the bell crank 9 is connected to the frame 1 via a vertical subarm 11. The vertical subarm 11 consists of upper and lower parts which are connected by a length-controller 12, and controlling the degree that the upper and lower parts are inserted into the length-controller 12 enables the whole length of the vertical subarm 11 to be changed. Such a bell crank 9, horizontal subarm 10 and vertical subarm 11 will never allow the bell crank 9 to rotate even when the retaining link mechanism 4 pivots about the rotational fulcrum S and will constantly maintain the distal end arm 7 vertical, thereby the supporting parallel link 8 which supports the operating microscope $W_1$, and other devices is also constantly maintained vertical.

The weight holding arm 6 which is extendedly formed backward from the second parallel link 3 has a moveably mounted counterweight $W_4$. Namely, the weight holding arm 6 is threaded so that the counterweight $W_4$ can be fitted thereon in a helical manner, thereby revolving the counterweight $W_4$ allows itself to be moved.

The retaining link mechanism 4 as constituted as above is secured to the frame 1 via a slide mechanism 13. The slide mechanism 13 comprises a fixing portion 15 which is pivotally mounted to the rotational fulcrum S on the frame 1 and has a rotatable continuous-thread screw 14 in a vertical manner, and a movable part 17 which is mounted to the retaining link mechanism 4 side and has a protrusion 16 which is fitted to the continuous-thread screw 14 in a helical manner. Therefore, rotating the continuous-thread screw 14 allows the retaining link mechanism 4 to move vertically with respect to the rotational fulcrum S. In coping with distance changes between the frame 1 and the bell crank 9 in accordance with the vertical movement of the retaining link mechanism 4, the length of the vertical subarm 11 is controlled by the length-controller 12.

Next, the balance conditions of the stand apparatus will be described. The description will be made including a premise that the total weight of the operating microscope $W_1$, side microscope $W_2$ and a video camera $W_3$, which are all supported at the distal end of the supporting arm 5, are referred to as operating microscope and other equipments with a symbol W $(=W_1+W_2+W_3)$ given. In order to stop the operating microscope and other equipments W at arbitrary positions in the air, the balance of the retaining link mechanism 4 needs to be adjusted both in horizontal and vertical directions as described above. Namely, when the horizontal distance from the rotational fulcrum S to the operating microscope and other equipments W is expressed as X, the horizontal distance from the rotational fulcrum S to the counterweight $W_4$ is expressed as $X_1$, the vertical distance from the rotational fulcrum S to the operating microscope and other equipments W is expressed as Y, and the vertical distance from the rotational fulcrum S to the counterweight $W_4$ is expressed as $Y_1$, the balanced status must meet the following equations;

Balance In horizontal direction: $W \times X = W_4 \times X_1$

Balance In vertical direction: $W \times Y = W_4 \times Y_1$

In this state, if the side microscope $W_2$ is removed and the retaining link mechanism 4 supports lighter operating microscope and other equipments as W minus $W_2$, it will be unbalanced and which needs to be corrected.

For the correction purpose, the counterweight $W_4$ is moved toward the operating microscope and other equipments as W minus $W_2$ by a distance of $X_2$ in order to be well balanced In the horizontal direction, the retaining link mechanism 4 is lifted by rotating the continuous-thread screw 14 so that the relative position of the rotational fulcrum S should be lowered by a distance of $Y_2$ with respect to the retaining link mechanism 4 in order to be well balanced in the vertical direction.

It is to be noted that the amounts of the above $X_2$ and $Y_2$ must meet the following equations;

Balance in horizontal direction: $(W-W_2) \times X = W_4 \times (X_1-X_2)$

Balance in vertical direction: $(W-W_2) \times (Y+Y_2) = W_4 \times (Y_1-Y_2)$

Figure 4:
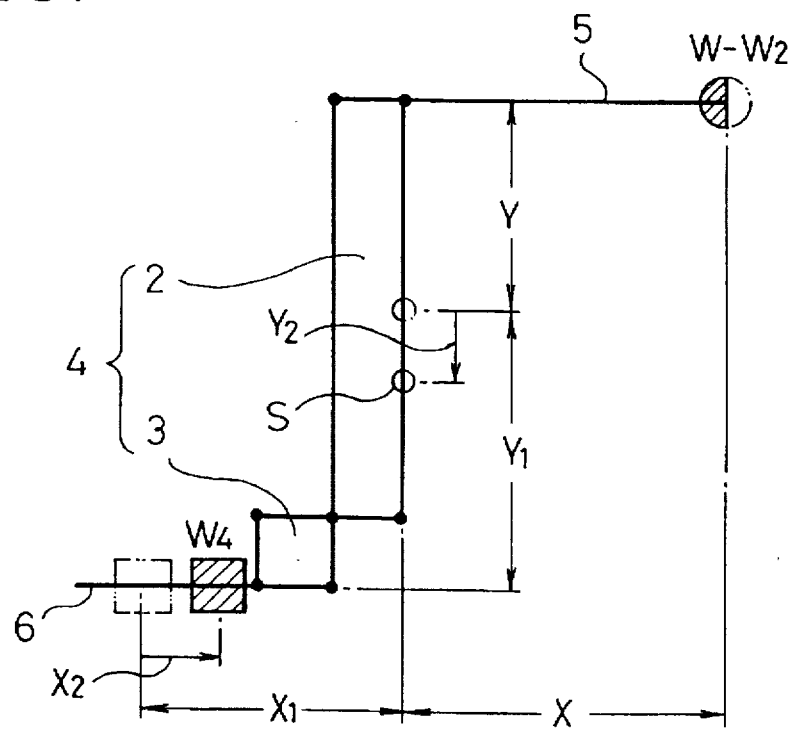
FIG. 4 is an explanatory view showing the total weight of the operating microscope and the video camera is balanced with a counterweight.

Although FIG. 4 shows that the vertical movement $Y_2$ of the retaining link mechanism 4 is about the same as the horizontal movement $X_2$ of the counterweight $W_4$, $Y_2$ is in fact substantially smaller than $X_2$, because movement of the whole retaining link mechanism 4 provides great balance-adjustment effect only with a slight movement.

In addition to the above description in which the counterweight $W_4$ is horizontally moved and the retaining link mechanism 4 is vertically moved, the counterweight $W_4$ and retaining link mechanism 4 may be vertically and horizontally moved, respectively.

While the frame 1 described in the above embodiment is of a floor type which is set on the floor, the frame 1 may be of a ceiling type which is suspended from the ceiling of the operating room.

Additionally, the "auxiliary devices" are not limited to a side microscope $W_2$ or video camera $W_3$, and any devices other than those are possible.

As described above, the stand apparatus according to the present invention requires only one counterweight, which eliminates a need to interlockedly move two counterweights simultaneously as conventionally, so that movement control of a counterweight is easy and a mechanism therefor can be simplified. Since vertical balancing is effected via a movement of the whole retaining link mechanism, even a slight movement can provide an effective balancing control. Therefore, an operation of balancing control is easy and reduced operational time required for balancing control is possible.

What is claimed is:

1. A stand apparatus for medical optical equipment, comprising:

an intermediary portion of a retaining link mechanism essentially consisting of first and second parallel links which interlock each other and mounted moveably in a vertical direction with respect to a rotational fulcrum of a frame, a supporting arm which is formed by extending a part of said first parallel link in a horizontal direction, said supporting arm retaining at the distal end thereof medical optical equipments and/or their auxiliary devices, and a weight holding arm which is formed by extending a part of said second parallel link in a horizontal direction opposite to said supporting arm, said weight holding arm being provided with a single counterweight that is movable with respect to the fulcrum such that all balance adjustment can be made by moving the single counterweight.

2. The stand apparatus for medical optical equipments according to claim 1, wherein said auxiliary devices include a side microscope.

3. The stand apparatus for medical optical equipments according to claim 1, wherein said auxiliary devices include a video camera.

4. The stand apparatus for medical optical equipments according to claim 1, wherein said auxiliary devices include a side microscope and a video camera.

5. The stand apparatus for medical optical equipments according to claim 1, wherein said frame is of a type which is set on a floor.

6. The stand apparatus for medical optical equipments according to claim 1, wherein said frame is of a type which is set on a floor.

7. A stand apparatus for medical optical equipment, comprising:

an intermediary portion of a retaining link mechanism essentially consisting of first and second parallel links which interlock each other and is mounted moveably in a horizontal direction with respect to a rotational fulcrum of a frame, a supporting arm which is formed by extending a part of said first parallel link in a horizontal direction, said supporting arm retaining at the distal end thereof medical optical equipments and/or their auxiliary devices, and a weight holding arm which is formed by extending a part of said second parallel link in a horizontal direction, said weight holding arm being provided with a single counterweight that is moveable with respect to the fulcrum such that all balance adjustments can be made by moving the single counterweight.

8. The stand apparatus for medical optical equipments according to claim 7, wherein said auxiliary devices include a side microscope.

9. The stand apparatus for medical optical equipments according to claim 7, wherein said auxiliary devices include a video camera.

10. The stand apparatus for medical optical equipments according to claim 7, wherein said auxiliary devices include a side microscope and a video camera.

11. The stand apparatus for medical optical equipments according to claim 7, wherein said frame is of a type which is set on a floor.

12. The stand apparatus for medical optical equipments according to claim 3, wherein said frame is of a type which is suspended from a ceiling of an operating room.

* * * * *